United States Patent [19]
Cronenberg

[11] 4,243,396
[45] Jan. 6, 1981

[54] HUMIDIFIER SEPARATOR

[75] Inventor: Richard A. Cronenberg, Ramsey, N.J.

[73] Assignee: Becton, Dickinson and Company, Paramus, N.J.

[21] Appl. No.: 30,127

[22] Filed: Apr. 16, 1979

Related U.S. Application Data

[63] Continuation of Ser. No. 856,397, Dec. 1, 1977, abandoned.

[51] Int. Cl.³ .......................................... A61M 11/02
[52] U.S. Cl. .................................. 55/238; 128/203.16;
239/338; 261/79 A; 261/78 A; 261/DIG. 65
[58] Field of Search .......... 261/79 A, 78 A, DIG. 65;
55/238, 257 C; 239/338; 128/193, 194

[56] References Cited

U.S. PATENT DOCUMENTS

| | | | |
|---|---|---|---|
| 3,206,175 | 9/1965 | Boteler | 239/338 |
| 3,248,860 | 5/1966 | Carlson | 55/257 C |
| 3,249,553 | 5/1966 | Steinberg | 239/338 |
| 3,326,538 | 6/1967 | Merritt | 55/238 |
| 3,358,413 | 12/1967 | Kalika | 55/238 |
| 3,572,660 | 3/1971 | Mahon | 261/78 A |
| 3,695,516 | 10/1972 | Rogers | 239/338 |
| 3,775,948 | 12/1973 | Beam | 55/257 C |
| 3,836,079 | 9/1974 | Huston | 239/338 |
| 3,903,884 | 9/1975 | Huston et al. | 261/DIG. 65 |
| 4,116,387 | 9/1978 | Kremer, Jr. et al. | 239/338 |

FOREIGN PATENT DOCUMENTS

| | | | |
|---|---|---|---|
| 123229 | 1/1947 | Australia | 239/338 |
| 1046264 | 12/1958 | Fed. Rep. of Germany | 239/338 |

*Primary Examiner*—Frank W. Lutter
*Assistant Examiner*—Gregory N. Clements
*Attorney, Agent, or Firm*—Kane, Dalsimer, Kane, Sullivan & Kurucz

[57] ABSTRACT

A separator adapted for use as part of a fluid dispenser system for supplying inhalable fluids and including a liquid source, a gas source, nozzle means, and supporting structure positioned so that gas from the gas source is directed by the nozzle means to aspirate liquid from the liquid source and cooperate therewith to form a desired mixture of liquid and gas. The separator includes an inner member having a radial surface extending therefrom. An outer casing surrounds a portion of the inner member and the radial surface extends into engagement with the outer casing and forms a tortuous passageway between the inner member and the outer casing. The separator is adapted to be positioned within the fluid dispenser system so that the mixture of liquid and gas passes along the tortuous passageway in the separator in contact with the radial surface whereupon the larger drops of liquid are removed from the mixture leaving a remaining mixture of desired consistency which passes from the separator and out of the dispenser for use.

6 Claims, 5 Drawing Figures

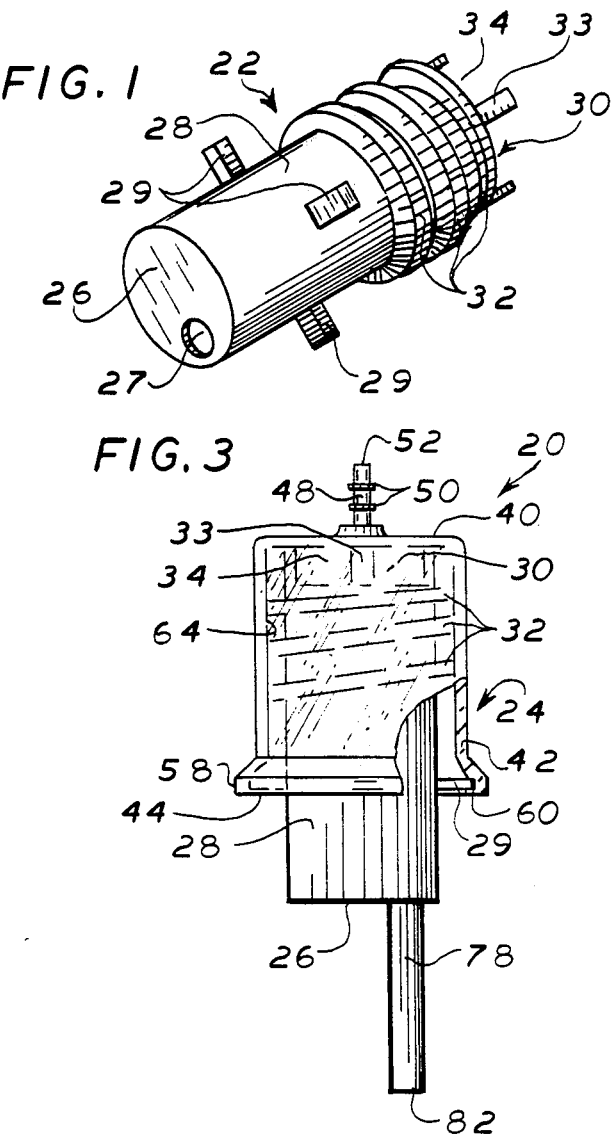
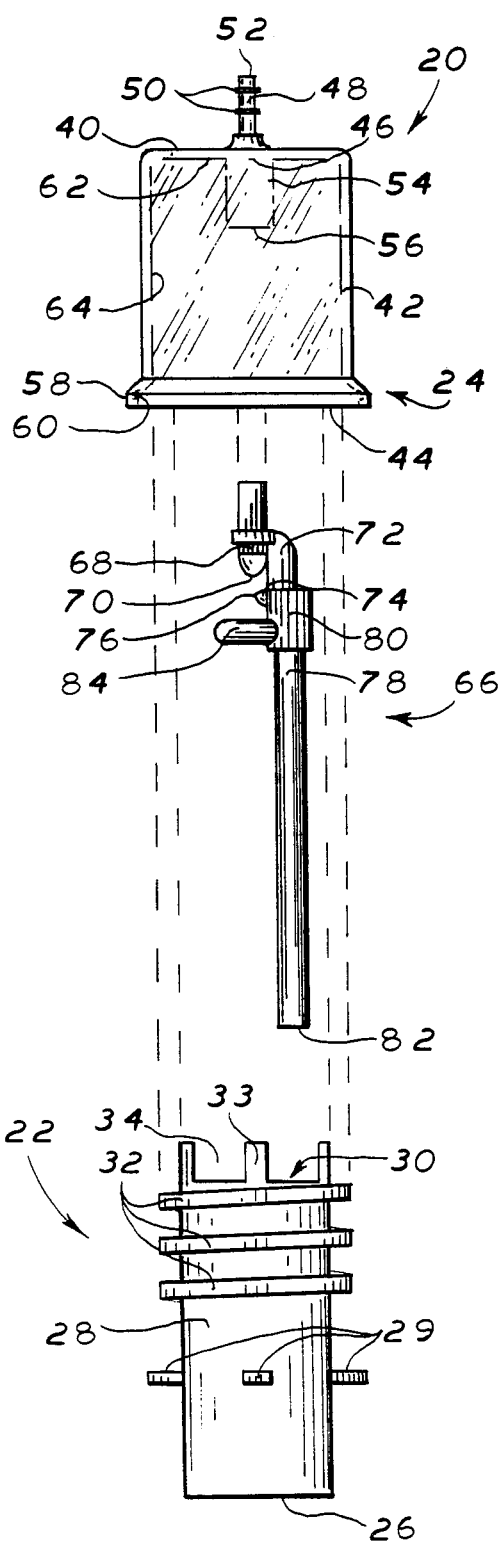
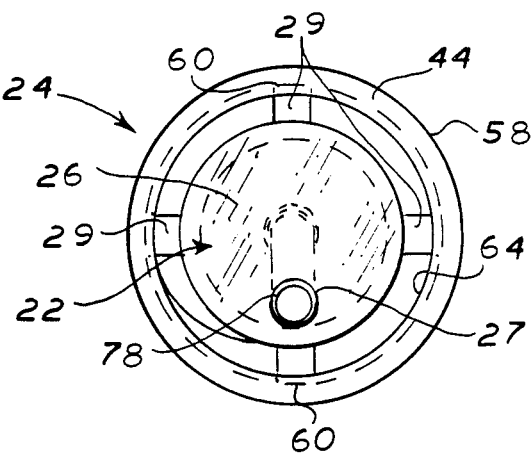

HUMIDIFIER SEPARATOR

This is a continuation of application Ser. No. 856,397, filed Dec. 1, 1977, now abandoned.

BACKGROUND OF THE INVENTION

There are many different types of nebulizers and humidifiers which employ a structure that facilitates the mixing of gas and vapor to supply a patient with an inhalable fluid mixture for breathing and medicinal purposes. It is common practice to provide a combination of oxygen and air and to subject this pure gas or a combination thereof to moisture so that the moisture is entrained in the gas flow path and the mixture is introduced to the patient. The vapor which is commonly used as the moistening agent is effective in easing the breathing of a person particularly one who is ill and has respiratory problems.

It is often difficult to achieve the desired vapor and avoid the presence of liquid droplets in the gas and liquid mixture. On the other hand, insufficient moisture in the gas does not produce the desired humidifying effect. Accordingly, it is most desirable to provide the best possible mixture of gas and vapor for the comfort of the patient.

In certain instances, a bubbling action is employed whereby the gas is bubbled through liquid and in that manner accumulates vapor as part of the mixture which is transferred from the humidifier to the patient. This type of system is noisy and can cause patient discomfort or irritation due to the noise. Accordingly, it is desirable to provide a humidifier which facilitates the formation of a mixture of gas and vapor for the most beneficial effect on a patient without undesirable noise associated with the use of the humidifier. An additional problem is patient discomfort due to droplets of liquid forming in the system which work their way through the system to the mask or nasal cannula directly connected to the patient's face. Accordingly, it is desirable to provide a humidifier which overcomes this difficulty as well.

The type of environment where the type of humidifier under consideration is most desirable is in the medical profession where a desired consistency of mixture of gas and vapor is introduced to a patient to ease breathing difficulties and in some cases to introduce medicaments which may be included in the vapor to the patient. It is always desirable with the type of humidifier under consideration to avoid the presence of droplets of liquid which indicates too much moisture and also the converse difficulty of lack of sufficient moisture so that virtually only gas is introduced to the patient which can cause irritation and potential breathing difficulties particularly over an extended period of time.

Examples of humidifiers with which this invention is applicable are depicted in U.S. Pat. Nos. 3,572,660; 3,874,379 and 3,836,079.

SUMMARY OF THE INVENTION

Among the primary objectives of the present invention is to provide a humidifier separator which is designed for use with a nebulizer nozzle to provide a mist of vapor including a mixture of a desired consistency of gas and liquid for introduction to a patient. In general, the gas is humidified to prevent the respiratory system from drying without providing a condition where an undesirable amount of liquid is introduced to the patient.

The structure is designed to utilize a helical surface along which the mixture of liquid and gas travels to permit separation of water droplets from the gaseous vapor so that humidified air without air borne water droplets is produced for introduction to the patient. The helical surface utilizes the velocity of the air spiraling through the threads of the helix to cause centrifugal force which pushes the water droplets out of the air and back into the water container.

Another objective of the invention is to provide a humidifier structure which is virtually silent thereby eliminating noisy conditions which is particularly useful in dealing with medical humidifier applications and avoiding patient discomfort or irritation due to excessive noise. Thus the best possible humidification of air or oxygen or a combination thereof is produced at a very low or negligible noise level.

A further objective is to provide a separator arrangement employing a helical surface therein which is adapted to be mounted in an existing humidifier structure, particularly one which employs a nozzle arrangement to provide a mixture of gas or liquid to form a gas and vapor mixture for introduction to a patient in a conventional fashion. The separator silently removes larger droplets from the mixture formed in the humidifier and returns these larger droplets back to the portion of the container housing the liquid. This type of separator is useful with humidifiers employing a nozzle arrangement to aspirate liquid and combine it with gas introduced under pressure to the humidifier to form the mixture. The container houses the fluid and has an inlet nozzle arrangement for introduction of the gas under pressure and an outlet arrangement for removal of the mixture of moisture and gas for introduction to the patient.

In summary, a separator is provided which is adapted for use as part of a fluid dispenser system for supplying inhalable fluids and including a liquid source, a gas source, mixing means, and supporting structure positioned so that gas from the gas source is directed by the mixing means to combine with liquid from the liquid source and cooperate therewith to form a desired mixture of liquid and gas. A separator includes an inner member having a radial surface extending therefrom. An outer casing surrounds a portion of the inner member and the radial surface extends into engagement with the outer casing and forms a tortuous passageway between the inner member and the outer casing. The separator is adapted to be positioned within the fluid dispenser system so that the mixture of liquid and gas passes along the tortuous passageway in the separator in contact with the radial surface whereupon the larger drops of liquid are removed from the mixture leaving a remaining mixture of desired consistency which passes from the separator and out of the dispenser for use.

With the above objectives among others in mind, reference is made to the attached drawings.

BRIEF DESCRIPTION OF THE DRAWINGS

In The Drawings:

FIG. 1 is a perspective view of the inner member of the separator of the invention;

FIG. 2 is an exploded side elevation view of the separator of the invention and nozzle arrangement employed therewith;

FIG. 3 is a partially sectional side elevation view of the components of FIG. 2 in assembled condition;

FIG. 4 is a bottom plan view thereof; and

DETAILED DESCRIPTION

Figure 5:
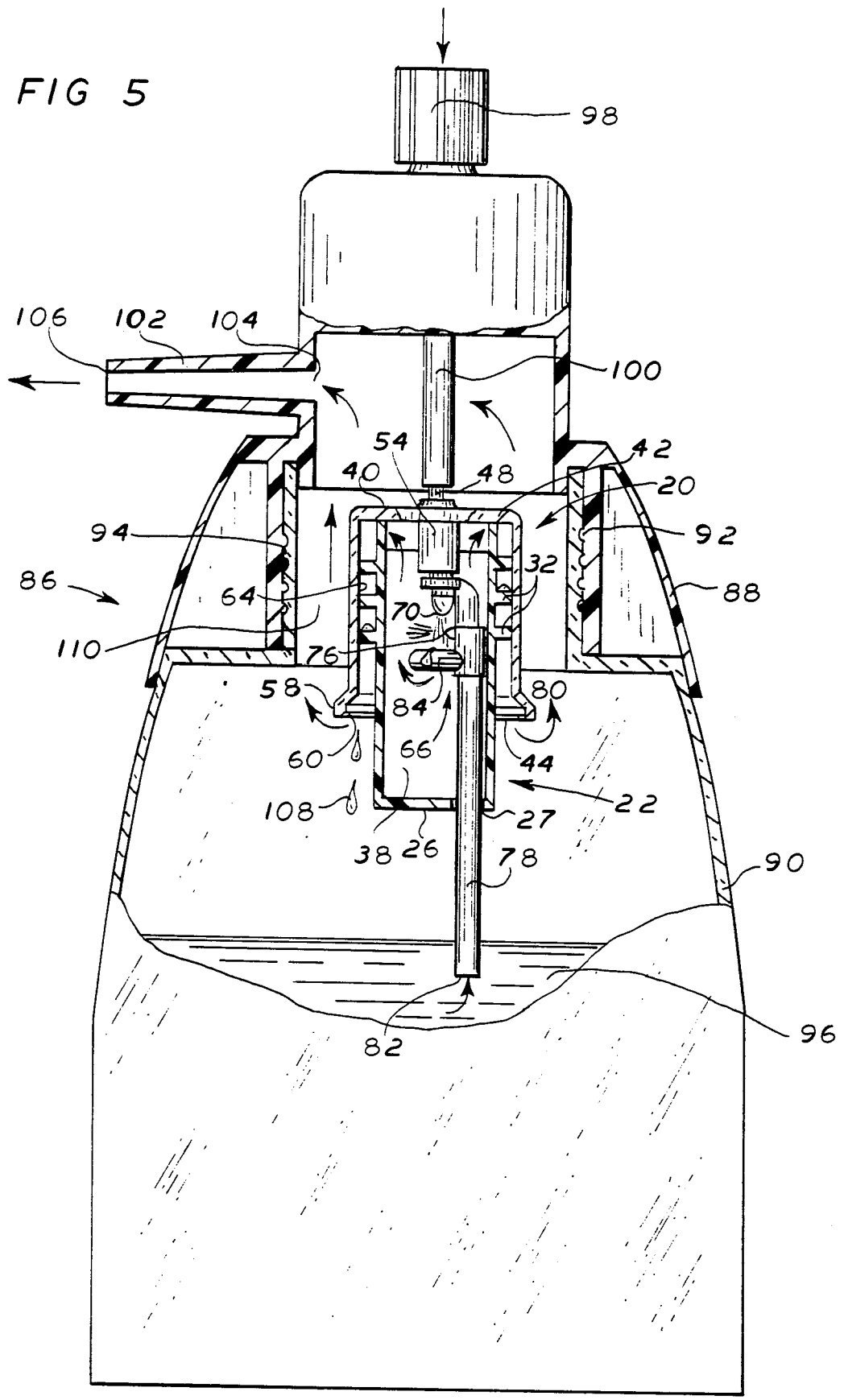
FIG. 5 is a partially sectional side elevation view of the separator of the invention mounted in a humidifier with arrows showing the direction of flow of gas, liquid, and a mixture thereof.

Separator 20 of the invention is depicted in exploded form in FIG. 2 and includes an inner member 22 and an outer casing 24. Inner member 22 includes a tubular inner portion with a base wall 26 and an upwardly extending annular side wall 28 terminating in an open top end 30. Extending along a portion of the length of side wall 28 is a radial surface in the form of a continuous helix 32. Other types of radial surfaces can also be utilized such as other spiral arrangements and arcuate passageways in place of the helix 32 to accomplish similar results achieved by the helix 32 as discussed in detail below. The helical surface formed by helix 32 is designed with a predetermined spacing and dimensional thickness so that a desired separation action is achieved. Inner member 22 is designed to work effectively in a conventional type humidifier in separating undesirable water droplets from a vapor/gas mixture to be introduced to a patient. Types of humidifiers that can be used include those of a conventional nature such as described in connection with U.S. Pat. Nos. 3,874,379; 3,572,660 and 3,836,079. The operating features of the structure in these patents are readily adaptable for use in the present system employing separator 20.

Open end 30 of inner member 22 is provided with a plurality of spaced upwardly extending lugs 33 which produce a plurality of openings 34 therebetween. Openings 34 provide the passageways between the interior and exterior of inner member 22. Additionally, base wall 26 is provided with an aperture 27 for introduction of a tube communicating with liquid in a container to introduce liquid to the interior chamber 38 in hollow inner member 22.

Also on the outer surface of inner member 22 are a plurality of spaced laterally extending tabs 29. The tabs 29 are positioned between the ends of tubular member 22 and are spaced from helix 32. These tabs 29 are provided to assist in locking inner member 22 with outer casing 24 in the manner described below. In the depicted embodiment, there are four tabs 29 and also four upwardly extending lugs 33 on inner member 22.

The other part of separator 20 is casing 24 and the casing has a top wall 40 and an annular side wall or skirt 42 depending therefrom. The side wall terminates in an open bottom end 44. A central passageway 46 is formed in upper wall 40 for introduction of gas. Extending upwardly from passageway 46 is a tubular connector 48 with annular ribs 50 on its outer surface to facilitate connection to the gas source. The connector 48 has an axial through passageway 52 which communicates with opening 46 in bottom wall 40 and with the hollow interior of a tubular housing 54 extending inwardly of the bottom wall to the interior of casing 24. Housing 54 has an open end 56 so that a through passageway is provided through interconnected connector 48, base wall 40 and tubular housing 54 for passage of gas therethrough into the interior of casing 24.

Connector 48 is designed for coupling with the interior of a cap structure of a humidifier as depicted in FIG. 5. Alternatively, the casing 24 can be formed as an integral part of the underside of a cap for a humidifier system such as that depicted in FIG. 5.

Surrounding open end 44 of casing 24 is a flange 58 formed with an annular recess 60 on its inner surface. Recess 60 is designed for coupling with tabs 29 of inner member 22 when the two parts are connected. Inner member 22 is extended through opening 44 in casing 24 and is directed toward base wall 40 until lugs 33 engage with the inner surface 62 of base wall 40. The outer diameter of helix 32 is predetermined so that it fits in snug engagement with the inner surface 64 of side wall 42 of the casing. Thus, the only travel path for materials within chamber 38 of inner member 22 out of the separator is through apertures 34 between lugs 33 and then along the helical surface of helix 32 and exiting through open end 44 of the casing. Inner member 22 is retained in coupled position with outer casing 24 by means of a "snap-in" interengagement between tabs 29 and recess 60 in flange 58. For this purpose, sufficient resilience is provided to the tabs 29 and the surfaces forming recess 60 to permit the slight deformation and then return to the relaxed position to achieve the "snap-in" effect. With the tabs 29 snapped into position in recess 60 and lugs 33 bottoming against surface 62 of base wall 40, the parts of separator 20 are in coupled interengagement.

The separator is designed to receive a nozzle and siphon tube assembly 66 when utilized with a conventional type of humidifier as depicted in FIG. 5. The nozzle and siphon tube arrangement includes a first vertical nozzle 68 which is mounted in frictional interengagement within housing 54 so that the passageway through the nozzle communicates with the passageway through base wall 40 of casing 24. In this manner gas can be introduced from a gas source directly to nozzle 68. Nozzle 68 has a nozzle orifice 70 pointed vertically downward within chamber 38. Coupled with nozzle 68 through interconnecting structure 72 is a lateral nozzle 74. The orifice 76 of lateral nozzle 74 is in alignment with the flow path exiting from nozzle orifice 70 of nozzle 68. Lateral nozzle 74 is in fluid communication with a siphon tube 78 through hollow interconnecting structure 80. Siphon tube 78 has an opening 82 at its free end for introduction into a reservoir of liquid. The hollow interconnecting structure 80 also includes a baffle 84 extending into alignment with the direction of flow from nozzle orifice 70. Lateral nozzle orifice 76 is located between nozzle orifice 70 and baffle 84 so that after gas passes from nozzle orifice 70 it will pass lateral orifice 76 and siphon liquid through siphon tube 78 and entrain the liquid with the gas to form a liquid/gas mixture. The liquid/gas mixture is then directed against baffle 84 which acts to break-up liquid droplets into smaller particles.

As stated above, one end of the siphon tube assembly 66 is mounted in position by frictionally engaging nozzle 68 with the inner surface of housing 54 in casing 24. The siphon tube 78 extends through opening 27 in base 26 of inner member 22. In this condition, the separator can be coupled with a conventional humidifier 86 as depicted in FIG. 5. The humidifier 86 includes a cap 88 in threaded interengagement with a reservoir or container 90. This is achieved by the threaded surface 92 of cap 88 interengaging with the threaded surface 94 on the neck of container 90. The container 90 includes a predetermined volume of liquid 96. The liquid can be water alone or mixed with a conventional medicament. The cap includes a threaded connector 98 at its upper end for connection to a conventional source of gas. Extending from connector 90 is a central hollow tube 100 which frictionally interengages with connector 48 of casing 24. In this manner, gas can pass through the cap structure and directly into interior chamber 38 of separator 20. The frictional interengagement between connector 48 and tube 100 mounts separator 20 in position in humidifier 86 with siphon tube 78 extending into the liquid 96.

The cap also contains a lateral outlet section in the form of a hollow tubular projection 102. An opening 104 at the inner end of tubular projection 102 communicates with the interior of humidifier 86 and the opening 106 at the other end of the tubular projection provides the exit for the desired mixture to be directed to the patient. A conventional connector can be mounted on the surface of projection 102 to direct the gas and vapor mixture exiting therefrom to the patient in the desired manner.

Humidifier 86, as depicted in FIG. 5, is one of a number of conventional types of humidifiers with which separator 20 is adapted for use. Humidifier 86 in the depicted embodiment is of the type which combines gas and water to provide a water vapor mixture for introduction to a patient. Connection to the source of oxygen and/or air is made with the use of connector 98 so that the oxygen and/or air is introduced to nozzle 68 at a predetermined pressure. Naturally the pressure can be varied to obtain the desired flow. A common pressure employed for the source of oxygen is 50 psig at the condition of maximum flow.

In use, the oxygen passes from nozzle orifice 70 toward baffle 84. As it passes lateral nozzle orifice 76, it creates a venturi effect so that water 96 is aspirated through siphon tube 78 to exit from nozzle orifice 76. The water combines with the oxygen and is entrained to form a mixture which is directed against baffle 84. Baffle 84 partially breaks up the water droplets to provide a mixture of water vapor in an intermediate condition.

This intermediate water vapor mixture is then free to exit through apertures 34 and into contact with helix 32. As the intermediate mixture passes along the helical surface of helix 32 in a spiral manner, the helix uses the velocity of the air spinning through the threads to cause centrifugal force to push further water droplets out of the mixture. These drops 108 are then free to fall from the end of helix 32 through opening 44 back into the volume of liquid 96 within container 90 for reuse. The remaining final mixture of gas and vapor, which is relatively free of liquid droplets, then passes to the opening 104 of outlet projection 102 through the open chambers 110 in cap 88 as depicted by the arrows in FIG. 5. As shown, this final mixture then passes through projection 102 out of the humidifier 86 and to the patient. This final mixture has the desired consistency with respect to relative moisture so that it is in the most beneficial condition for introduction to the patient. The system is operated on a very low noise level thereby avoiding patient discomfort or irritation while also providing excellent humidification of the air.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. A hand size separator for a medical fluid dispenser system for supplying inhalable fluids, the system including a liquid source, a gas source and supporting structure, the separator comprising:

means for connection to a source of gas;
means for connection to a source of liquid;
a hollow inner member having a helical radial surface extending outwardly therefrom;
an outer casing surrounding a portion of the inner member and the helical radial surface extending into engagement with the inner surface of the outer casing so as to form a tortuous passageway therebetween communicating with an opening to the exterior of the separator;
a nozzle mounted within the hollow interior of the inner member and positioned to be in communication with the means for connection to a source of gas and means for connection to a source of liquid so that when the separator is connected to a source of gas and a source of liquid gas will be directed by the nozzle to aspirate liquid and cooperate therewith to form a desired mixture of liquid and gas;
surfaces on the inner member and the outer member forming a passageway between the hollow interior of the inner member and the exterior thereof so that the mixture of gas and liquid produced within the inner member is directed into engagement with the helical radial surface between the inner and outer members and the mixture passes along the tortuous passageway in the separator in contact with the radial surface whereupon the larger droplets of liquid are removed from the mixture for drainage through the opening to the exterior of the separator leaving a remaining mixture of desired consistency to be supplied to a patient;
the separator being mounted in a liquid container to form a nebulizer or humidifier for introducing therapeutic fluids to a patient;
the liquid container having an inlet section and an outlet section;
the inlet section having means thereon for removable connection to a source of gas and the liquid container having a reservoir of liquid therein forming a source of liquid;
the nozzle of the separator positioned in the liquid container in communication with the liquid therein and positioned with respect to the inlet section so that gas entering the container is directed to the nozzle through the means on the separator for connection to a source of gas thereby permitting the nozzle to aspirate liquid from the container and cooperate in formation of a mixture of liquid and gas;
the separator being positioned in the liquid container in a position so that the mixture of desired consistency communicates with the outlet section of the container for passage therethrough for transmittal to the patient;
the liquid container including a hollow base for housing the liquid with an open top end and a removable cap coupled with the open top end of the base, the separator being removably mounted in the cap, the inlet section being located in the cap; and
the separator being positioned in the container so that the separated drops of liquid exiting from the tortuous path will fall by gravity through the opening to the exterior of the separator and drain into the reservoir of the liquid container for reuse.

2. The invention in accordance with claim 1 wherein the outer casing is tubular to form an annular side wall and has a base wall at one end of the side wall and is open at the end opposite to the base wall, the helical radial surface terminating at the open end of the outer casing which forms the opening to the exterior of the separator which is in communication with the end of the tortuous passageway between the inner member and the outer casing.

3. The invention in accordance with claim 2 wherein the inner member positioned in the outer casing is provided with an open upper end adjacent the base wall of the casing and a lower end wall, an aperture in the base wall of the casing for introduction of gas from a gas source when connected with the separator for mixing with liquid aspirated by the nozzle when the separator is interconnected with a source of liquid, the liquid being water and the gas being at least one of oxygen and air, and the separator being formed of disposable plastic material.

4. The invention in accordance with claim 3 wherein a plurality of spaced lugs extend upwardly from the upper end of the inner member into engagement with the casing, the spaces between the lugs forming apertures to provide a passageway from the interior of the inner member to the exterior thereof into communication with the helical radial surface, a plurality of spaced radial tabs extending from the outer surface of the inner member intermediate the ends thereof, an annular recess on the inner surface of the casing in position for alignment with the radial tabs on the outer surface of the inner member, and the tabs and casing having sufficient resilience therebetween so that the tabs can snap into position in the annular recess thereby coupling the inner member and outer casing together.

5. The invention in accordance with claim 4 wherein the nozzle includes a first nozzle means thereon for connection to a source of gas, the first nozzle means being mounted in the hollow interior of the inner member and positioned to direct gas introduced under pressure therethrough in a downward direction, the nozzle including a second nozzle means positioned perpendicular to the first nozzle means in the hollow interior of the inner member and adjacent to the first nozzle means for the eduction of a spray of liquid therefrom, a siphon tube in fluid communication with the second nozzle means and extending downwardly and outwardly of the inner member with means thereon to bring the siphon tube into fluid communication with a liquid source, and a baffle member adjacently below said first and second nozzle means onto which the spray of the mixture of liquid in gases to be directed to nebulize the same prior to exit of the mixture from the hollow interior of the inner member into communication with the radial surface.

6. The invention in accordance with claim 1 wherein the helical surface is continuous about the outer surface of the inner member.

* * * * *